United States Patent
Algotsson et al.

(10) Patent No.: US 7,294,743 B2
(45) Date of Patent: Nov. 13, 2007

(54) METHOD FOR SYNTHESIS OF ACRYLAMIDE DERIVATIVES

(75) Inventors: Mattias Algotsson, Uppsala (SE); Philippe Busson, Uppsala (SE); Nicolas Thevenin, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 126 days.

(21) Appl. No.: 10/572,294

(22) PCT Filed: Oct. 18, 2004

(86) PCT No.: PCT/SE2004/001498

§ 371 (c)(1), (2), (4) Date: Mar. 14, 2006

(87) PCT Pub. No.: WO2005/040092

PCT Pub. Date: May 6, 2005

(65) Prior Publication Data

US 2007/0106090 A1    May 10, 2007

(30) Foreign Application Priority Data

Oct. 23, 2003   (SE)   .................................... 0302827

(51) Int. Cl.
*C07C 233/10*   (2006.01)
(52) U.S. Cl. ..................................................... 564/204
(58) Field of Classification Search ................. 564/204
See application file for complete search history.

(56) References Cited

U.S. PATENT DOCUMENTS 4,130,470 A    12/1978   Rosengren et al.
7,060,776 B2 *  6/2006   Algotsson et al. ....... 526/307.3

FOREIGN PATENT DOCUMENTS

WO    WO 02/25264    3/2002

* cited by examiner

*Primary Examiner*—Shailendra Kumar
(74) *Attorney, Agent, or Firm*—Yonggang Ji

(57) ABSTRACT

The present invention relates to a method for synthesis of an acrylamide derivative, starting with dissolving a salt of a nucleophilic amine in water to form an aqueous solution and desalting said solution with a base, comprising the following steps:
a) addition of dissolved activated acrylic acid derivative to said solution;
b) acidification of aqueous phase; and
c) extraction of said aqueous phase.

12 Claims, No Drawings

METHOD FOR SYNTHESIS OF ACRYLAMIDE DERIVATIVES

CROSS REFERENCE TO RELATED APPLICATIONS

This application is a filing under 35 U.S.C. § 371 and claims priority to international patent application number PCT/SE2004/001498 filed Oct. 18, 2004, published on May 6, 2005, as WO 2005/040092, which claims priority to application number 0302827-1 filed in Sweden on Oct. 23, 2003; the disclosure of which are incorporated herein by reference in their entireties.

BACKGROUND OF THE INVENTION

The present invention relates to a method for synthesis of acrylamide derivatives, preferably immobilines. The method is especially suitable for synthesis of the immobiline acrylamido agmatine but may be used for synthesis of any acrylamide derivative. The compounds synthesised by the method can be used in the production of a separation material. A preferred example is a separation material for separating amphoteric compounds based on differences in isoelectric points (pI), in particular by electrophoresis (isoelectric focusing, IEF). Another preferred example is a separation material for 2D electrophoresis.

In two-dimensional, 2D, electrophoresis substances are separated in two dimensions. In the first dimension, the substances are separated by isolectric focusing. Isoelectric focusing is often followed by a second dimension of gel electrophoresis in which each separated substance is further separated according to molecular weight and/or molecular size. Isoelectric focusing and gel electrophoresis is typically run in two dimensions which are perpendicular to each other. 2D electrophoresis can be run both in analytical and preparative amounts of substances to be separated.

The substances to be separated are typically bio-organic and encompass primarily compounds having polypeptide structure and/or carbohydrate structure. Proteins are particularly important.

In certain kinds of electrophoresis the carrier material has been functionalized with groups which provide conditions that are beneficial for the intended separation. One important kind of groups has been pH-buffering groups. By immobilising pH-buffering groups of different pKa's between the anode end and the cathode end of an electrophoretic gel it became possible during the late seventies to set up immobilised pH-gradients (Aminkemi, U.S. Pat. No. 4,130,470) to be used in isoelectric focusing. In order to have good pH-gradients it was important to have a range of different pH-buffering groups with increasing/decreasing pKa values spaced within a desired pH-interval. The difference between the pKa of two neighbouring buffering groups has typically been 1-2 pH units. For pH intervals extending above pH 10 there has been described a charged carrier material in WO 02/25264 (Amersham Biosciences) having improved stability against hydrolysis at pH>10 for the manufacture of separation materials. This document describes (1) properly selecting immobilised pH-buffering groups amongst those that have
   (a) a pH-dependent charge on a nitrogen atom which binds to an $sp^2$-hybridised carbon atom, and
   (b) a pKa≧9.5, e.g. ≧10.0 or ≧10.5 or ≧11.0, and/or (2) utilising carrier materials, which have been based on certain acryl monomers.

Immobilines are acrylamide derivatives with buffering groups. Immobilines are weak acids or bases defined by their pK value. A preferred use of the immobilines is for 2D electrophoresis. One of the most interesting immobilines is acrylamido agmatine. The synthesis of acrylamido agmatine as described in WO 02/25264 involves the reaction of agmatine sulphate and barium hydroxide in water. Thereafter, the formed precipitate of barium sulphate has to be removed by filtration and desalted agmatine is obtained by freeze drying of the aqueous phase. To get rid of most of the barium sulphate, a precipitation has to be repeated at least once. Next step is redissolving desalted agmatine in an organic solvent and addition of acryloyl chloride and a base. The reaction is time consuming and often gives poor yield and purity. Furthermore, the work-up of the reaction mixture often faces difficulties to remove the base and the excess of unreacted acryloyl chloride (often hydrolysed to acrylic acid during the course of reaction).

Acrylamido agmatine has a theoretical pKa value of 13.52 and suitable for preparation of separation materials for separation in pH intervals extending 10.

BRIEF SUMMARY OF THE INVENTION

The present invention relates to a simple method for synthesis of any acrylamide derivatives, preferably immobilines, which method avoids the above mentioned drawbacks.

Furthermore, the invention relates to a method for production of new acrylamide derivatives (immobilines) which fill the gaps in the previously known immobiline family.

A preferred immobiline produced with the method of the invention is acrylamido agmatine. However, the method of the invention is applicable to any acrylamide derivative, especially for production of hydrophilic immobilines with high pKa, such as pKa>10.

Preferably, the immobilines are used in an isoelectric focusing separation material containing an immobilised pH gradient. The separation material comprises immobilines, produced by the method of the invention, for defining at least a part of the pH interval of the gradient. Preferably, the gradient/interval extends to pH>10 with immobilines having pKa≧9.5, e.g. ≧10.0 or ≧10.5 or ≧11.0, being included. Preferably, the electrophoretic separation method is 2D electrophoresis.

The present invention provides a general method for synthesis of any acrylamide derivative, starting with dissolving a salt of a nucleophilic amine in water to form an aqueous solution and desalting said solution with a base, comprising the following steps:

a) addition of dissolved activated acrylic acid derivative to said solution;

b) acidification of aqueous phase; and c) extraction of said aqueous phase.

Preferred acrylamide derivatives are immobilines. A preferred immobiline is acrylamido agmatine.

For production of acrylamido agmatine it is preferred to start with an agmatine salt, preferably with agmatine sulphate.

In a preferred embodiment the extraction in step c) is done with an organic solvent, preferably with methyl isobutyl ketone (MIBK).

The acrylic acid derivative is an activated acrylic acid derivative selected from the group acryloyl chloride, acrylic acid N-hydroxysuccinimide ester, pentafluorophenyl acrylate, pentachlorophenylacrylate, 4-nitrophenyl acrylate, etc.

According to the invention the desalting of agmatine sulphate or any other salt of a nucleophilic amine is with any organic base, preferably triethylamine (TEA) and diisopropylethylamine (DIPEA), or any inorganic base, preferably sodium hydroxide (NaOH) and potassium carbonate ($K_2CO_3$).

In a preferred embodiment the method further comprises fixing pH to about 7.

In an alternative embodiment the method comprises, before step b), i) basification of aqueous phase to a pH above the pKa of the organic base, and ii) extraction of aqueous phase with an organic solvent to remove the organic base.

According to the preferred method of the invention agmatine sulphate is dissolved, desalted with $K_2CO_3$ and the method comprises the following steps:

a) addition of acryloyl chloride;

b) acidification to pH 1-4, preferably pH 2.3;

c) filtration d) extraction with MIBK;

e) pH adjustment to pH 7

DETAILED DESCRIPTION OF THE INVENTION

The novel method for synthesis of acrylamide derivatives according to the invention is solving all the problems within prior art such as problem with reproducibility and problems related to health aspects. According to the invention NaOH, TEA, DIPEA or $K_2CO_3$ was used as base to desalt the starting material and to capture as well the proton liberated during the reaction between acryloyl chloride and the desalted starting material. The work-up of the reaction was improved giving high purity, high yield and allowing an easy scaling-up. The excess of acryloyl chloride, which is necessary for the reaction to proceed to excellent yield and which hydrolyses to acrylic acid during the course of reaction, is removed from the aqueous phase by extraction using MIBK after acidification of the aqueous phase. This synthetic approach can be easily applied to the preparation of other immobilines for which the contaminating acrylic acid is a critical parameter when using those materials for preparation of 2D electrophoresis gels.

The method according to the invention offers multiple variations in the choice of the different components and is ruled by the type of free amine which has to be coupled to acryloyl chloride or any activated acrylic acid derivative (acrylic acid N-hydroxysuccinimide ester, pentafluorophenyl acrylate, pentachlorophenyl acrylate, 4-nitrophenyl acrylate, etc).

The method according to the invention offers novel opportunities for the preparation of acrylamide derivatives. A specific application is the preparation of immobilines for 2D electrophoresis which is shown in the experimental part below. Immobilines with high pKa value are especially interesting.

However, the method is not limited to immobiline production but can be used for other purposes involving preparation of acrylamide derivatives. Examples of acrylamides are based on unsubstituted and/or N-alkyl substituted acrylamides or methacrylamides.

The invention will now be illustrated with a number of non-limiting patent examples. The invention is defined in more details in the appending claims.

EXAMPLES

Below, the present invention will be described by way of examples, which are provided for illustrative purposes only and accordingly are not to be construed as limiting the scope of the present invention as defined by the appended claims. All references given below and elsewhere in this application are hereby included herein by reference.

I. Synthesis of Acrylamidoagmatine

The chemical structure of acrylamido agmatine is shown in FIG. 1.

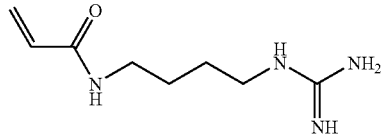

FIG. 1

A. Using NaOH as a Base

Agmatine sulphate (2.28 g, 10 mmol) was dissolved in distilled water (20 ml) in a three-necked round-bottom flask (50 ml) equipped with a magnetic stirrer and a pH meter. The reaction mixture was cooled down on an ice-bath.

For desalting, sodium hydroxide (NaOH) (1M) was added to the round-bottomed flask until pH=12 was obtained. Acryloyl chloride (1.36 g, 1.22 ml, 15 mmol), dissolved in acetone (5 ml), was added drop wise to the flask. The pH of the reaction mixture was maintained at 11.8 during the addition of the acryloyl chloride solution using NaOH (1M). The reaction was allowed to proceed at RT for 2 h. The stirring was then stopped. The pH of the aqueous phase was then fixed to pH 2.5 by addition of concentrated sulphuric acid. The aqueous phase (about 40 ml) was then extracted with MIBK (methyl isobutyl ketone)(3 times 80 ml) to remove excess acrylic acid formed during the reaction. The traces of MIBK were evaporated on a rotary evaporator to yield the product in water. The yield was at least 50%.

B. Using TEA as a Base

Agmatine sulphate (2.28 g, 10 mmol) was dissolved in distilled water (15 ml) in a round-bottom flask (50 ml) equipped with a magnetic stirrer. Triethylamine (TEA) (3.52 ml, 25 mmol) was added to the round-bottom flask. The reaction mixture was cooled down on an ice-bath and the mixture was stirred for 10 minutes at 5° C. Acryloyl chloride (1.36 g, 1.29 ml, 15 mmol), dissolved in acetone (5 ml), was added drop wise to the flask using a Pasteur-pipette. The reaction was allowed to proceed at 5° C. for 1 h. The stirring was then stopped. $K_2CO_3$ was added to the round-bottom flask until the pH was settled to 11. The volume of the aqueous phase was then 75 ml. The aqueous phase was then extracted with MIBK (2 times 150 ml) to remove TEA. The pH of the aqueous phase was then fixed to pH 2.3 by addition of concentrated sulphuric acid. The aqueous phase was then extracted with MIBK (3 times 150 ml) to remove excess acrylic acid formed during the reaction. The pH of the aqueous phase was then fixed to pH 7 by addition of $K_2CO_3$. The yield was at least 95%.

Optionally, the water could be removed by freeze-drying but this increased the risk of homopolymerization of the acrylamido agmatine. However, if this step is performed, the final white powder can be dissolved in isopropanol and filtered to remove the polymer eventually formed and the salts still present in the aqueous phase.

C. Using DIPEA as a Base

Agmatine sulphate (2.28 g, 10 mmol) was dissolved in distilled water (10 ml) in a round-bottom flask (50 ml) equipped with a magnetic stirrer. Diisopropylethyldiamine (DIPEA) (3.88 g, 5.23 ml, 20 mmol) was added to the round-bottom flask together with acetone (10 ml). The reaction mixture was cooled down on an ice-bath and the mixture was stirred for 10 minutes at 5° C. Acryloyl chloride (1.81 g, 1.625 ml, 20 mmol), dissolved in acetone (5 ml), was added drop wise to the flask using a Pasteur-pipette. The reaction was allowed to proceed at 5° C. for 1 h. The stirring was then stopped. $K_2CO_3$ was added to the round-bottom flask until the pH was settled to 12. The volume of the aqueous phase was then 75 ml. The aqueous phase was then extracted with MIBK (2 times 150 ml) to remove DIPEA. The pH of the aqueous phase was then fixed to pH 2.3 by addition of concentrated sulphuric acid. The aqueous phase was then extracted with MIBK (3 times 150 ml) to remove excess acrylic acid formed during the reaction. The pH of the aqueous phase was then fixed to pH 7 by addition of $K_2CO_3$. The yield was at least 95%.

Optionally, the water could be removed by freeze-drying but this increased the risk of homopolymerization of the acrylamidoagmatine. However, if this step is performed, the final white powder can be dissolved in isopropanol and filtered to remove the polymer eventually formed and the salts still present in the aqueous phase.

D. Using $K_2CO_3$ as a Base

Using $K_2CO_3$ as a base is the best mode to perform the invention. Agmatine sulphate (2.28 g, 10 mmol) was dissolved in distilled water (5 ml) in a round-bottom flask (50 ml) equipped with a magnetic stirrer. $K_2CO_3$ (4.14 g, 30 mmol), dissolved in distilled water (5 ml), was added to the round-bottom flask. The reaction mixture was cooled down on an ice-bath and the mixture was stirred for 10 minutes at 5° C. Acryloyl chloride (1.81 g, 1.625 ml, 20 mmol), dissolved in acetone (5 ml), was added drop wise to the flask using a Pasteur-pipette. The reaction was allowed to proceed at 5° C. for 1 h.

The stirring was then stopped. The aqueous phase was then fixed to pH 2.3 with concentrated sulphuric acid and filtered on a glass filter. The aqueous phase was then extracted with MIBK (2 times 100 ml) to remove excess acrylic acid formed during the reaction. The pH of the aqueous phase was then fixed to pH 7 by addition of $K_2CO_3$. The yield was at least 95%.

Optionally, the water could be removed by freeze-drying but this increased the risk of homopolymerization of the acrylamido agmatine. However, if this step is performed, the final white powder can be dissolved in isopropanol and filtered to remove the polymer eventually formed and the salts still present in the aqueous phase.

II. Use of Acrylamide Derivatives Produced According to the Invention

A preferred use is for immobiline production, especially acrylamido agmatine, see above. The immobilines are used in, for example, production of 2D gels. The invention also relates to use of acrylamide derivatives as carriers in other electrophoretic applications.

Furthermore, the acrylamide derivatives can be used in the production of chromatographic beads and other chromatographic supports.

A further use of acrylamide derivatives are as flocculating agents.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method for synthesis of an acrylamide derivative, starting with dissolving a salt of a nucleophilic amine in water to form an aqueous solution and desalting said solution with a base, comprising the following steps:
    a) addition of dissolved activated acrylic acid derivative to said solution;
    b) acidification of aqueous phase; and
    c) extraction of said aqueous phase.

2. The method of claim 1, wherein the acrylamide derivative is an immobiline.

3. The method of claim 2, wherein the acrylamide derivative is acrylamido agmatine.

4. The method of claim 3, wherein the salt is an agmatine salt.

5. The method of claim 1, wherein the extraction in step c) is performed with an organic solvent.

6. The method of claim 5, wherein the organic solvent is MIBK (methyl isobutyl ketone).

7. The method of claim 1, wherein the acrylic acid derivative is an activated acrylic acid derivative selected from the group consisting of acryloyl chloride, acrylic acid N-hydroxysuccinimide ester, pentafluorophenyl acrylate, pentachlorophenylacrylate, and 4-nitrophenyl acrylate.

8. The method of claim 1, wherein the desalting is with NaOH, TEA (triethylamine), DIPEA (diisopropylethylamine), or $K_2CO_3$.

9. The method of claim 1, further comprising fixing pH to 7.

10. The method of claim 1, comprising, before step b),
    i) basification of aqueous phase to a pH above the pKa of the organic base, and
    ii) extraction of aqueous phase with an organic solvent to remove the organic base.

11. The method of claim 1, wherein agmatine sulphate is dissolved, desalted with $K_2CO_3$ and comprising the following steps:
    a) addition of acryloyl chloride;
    b) acidification to pH 1-4;
    c) filtration;
    d) extraction with MIBK; and
    e) pH adjustment to pH 7.

12. The method of claim 11, wherein the acidification pH is 2.3.

* * * * *